(12) United States Patent
Moran

(10) Patent No.: US 6,496,998 B2
(45) Date of Patent: Dec. 24, 2002

(54) PROTON MOTIVE FORCE TOOTHBRUSH

(75) Inventor: Francis Xavier Moran, 71 College Ave., West Somerville, MA (US) 02144

(73) Assignee: Francis Xavier Moran, Somerville, MA (US)

( * ) Notice: Subject to any disclaimer, the term of this patent is extended or adjusted under 35 U.S.C. 154(b) by 0 days.

(21) Appl. No.: 09/816,190

(22) Filed: Mar. 26, 2001

(65) Prior Publication Data

US 2002/0177107 A1 Nov. 28, 2002

Related U.S. Application Data

(60) Provisional application No. 60/227,267, filed on Aug. 24, 2000.

(51) Int. Cl.$^7$ .................................................. A46B 9/04

(52) U.S. Cl. ......................... 15/105; 15/167.1; 604/20

(58) Field of Search ............................... 15/105, 167.1; 604/20

(56) References Cited

U.S. PATENT DOCUMENTS

| 3,840,795 | A | * | 10/1974 | Roszyk |
| 4,665,921 | A | * | 5/1987 | Teranishi |
| 4,944,296 | A | * | 7/1990 | Suyama |
| 5,704,087 | A | * | 1/1998 | Strub |
| 5,876,207 | A | * | 3/1999 | Sundius |
| 5,894,453 | A | * | 4/1999 | Pond |

FOREIGN PATENT DOCUMENTS

| JP | 5-76549 | * | 3/1993 |

OTHER PUBLICATIONS

Metzler, DE. *Biochemistry: The Chemical Reactions of Living Cells* New York: Academic Press. (1977) p 444–464.
Walsh CT. "Enzymes in the D–alanine Branch of Bacterial Cell Wall Peptidoglycan Assembly." *J Biol Chem* (1989) Feb. 15;264(5):2393–6.
Shockman GD, Barrett JF. "Structure, Function, and Assembly of Cell Walls of Gram–Positive Bacteria." *Annu Rev Microbiol* (1983) 37:501–27.
Eisenberg D. "Three–Dimensional Structure of Membrane and Surface Proteins." *Annu Rev Biochem* (1984) 53:595–623.
Singer SJ, Nicolson GL. "The Fluid Mosaic Model of the Structure of Cell Membranes." *Science* (1972) Feb 18; 175(23):720–31.
Unwin N, Henderson R. "The Structure of Proteins in Biological Membranes." *Sci Am* (1984) Feb;250(2):78–94.
Mitchell P. "Keilin's Respiratory Chain Concept and its Chemiosmotic Consequences." *Science* (1979) Dec. 7; 206(4423):1148–59.

(List continued on next page.)

*Primary Examiner*—Randall E. Chin
(74) *Attorney, Agent, or Firm*—Medlen & Carroll, LLP

(57) ABSTRACT

The present invention is used to obtund tooth decay and periodontal lesions by obstructing the proton motive force that exists in bacteria. The result is that glycolysis, DNA synthesis and chelation is upset and this will cause bacteria to dissolute logrithmically. The invention is also used to harden and remineralize enamel and dentin by using fluoride compounds available in over-the-counter dental cleansers. The invention takes into consideration the vector magnitude of the hydration layer between the enamel and the pellicle plaque layer of teeth which insulates the teeth from the electrical potentials of electrophoresis. The claim that electrical potentials can be placed on teeth does not take this physico-chemical phenomenon into consideration. This invention uses the proper voltage to produce ionization of molecules in a salivary slurry of gels, dentrifice's and rinses.

5 Claims, 3 Drawing Sheets

OTHER PUBLICATIONS

Taniguchi K, Suzuki K, Kai D, Matsuoka I, Tomita K, Iida S. "Conformational Change of Sodium– and Potassium–Dependent Adenosine Triphosphatase. Conformational Evidence for the Post–Albers Mechanism in Na+– and K+–Dependent Hydrolysis of ATP." *J Biol Chem.*(1984) Dec. 25; 259(24):15228–33.

Hatefi Y. "The Mitochondrial Electron Transport and Oxidative Phosphorylation System." *Annu Rev Biochem.* (1985) 54:1015–69.

Naqui A, Chance B, Cadenas E. "Reactive Oxygen Intermediates in Biochemistry." *Annu Rev Biochem.* (1986) 55:137–66.

Boyer PD. "The Unusual Enzymology of ATP Synthase." *Biochemistry* (1987) Dec. 29;26(26):8503–7.

Chernyak BV. Kozlov IA. "Regulation of H+ –ATPases in Oxidative– and Photophosphorylation." *Trends Biochem Sci.* (1986) Jan.;11:32–35.

Prince RC. "The Proton Pump of Cytochrome Oxidase." *Trends Biochem Sci.* (1988) May;13(5):159–60.

Featherstone JDR. Goodman P. MacLean JD. "Electron Microscope Study Of The Defect Zones In Dental Enamel." *J Ultrastructural Research.* (1979) 67:117–123.

Nelson DG, McLean JD. "High–Resolution Electron Microscopy of Octacalcium Phosphate and its Hydrolysis Products." *Calcif Tissue Int.* (1984) Mar.;36(2):219–32.

Nelson DG, Featherstone JD, Duncan JF, Cutress TW. "Effect of Carbonate and Fluoride on the Dissolution Behaviour of Synthetic Apatites." *Caries Res* (1983) 17(3):200–11.

LeGeros RZ, Trautz OR, Klein E, LeGeros JP. "Two Types of Carbonate Substitution in the Apatite Structure." *Experientia.* (1969) Jan. 15;25(1):5–7.

Featherstone JD, Mayer I, Driessens FC, Verbeeck RM, Heijligers HJ. "Synthetic Apatites Containing Na, Mg, and CO3 and Their Comparison With Tooth Enamel Mineral." *Calcif Tissue Int* (1983) 35(2):169–71.

Moreno EC, Kresak M, Zahradnik RT. "Physicochemical Aspects of Fluoride–Apatite Systems Relevant to the Study of Dental Caries." *Caries Res* (1977) 11 Suppl 1:142–71.

Zahradnick RT, Moreno EC, Propas D. "Enamel Demineralization By Streptococcus Mutans In The Presence Of Salivary Pellicle" *J Dental Res* (1977) 56:1107–1110.

Krasse B. "Biological Factors as Indicators of Future Caries." *Int Dent J* (1988) Dec.;38(4):219–25.

Margolis HC, Moreno EC. "Kinetic and Thermodynamic Aspects Of Enamel Demineralization." *Caries Res* (1985) 19:22–35.

Besic FC. "Carieslike Enamel Changes by Chemical Means." *J Dent Res* (1953) Dec.;32:830–839.

Alaluusua S, Kleemola–Kujala E, Nystrom M, Evalahti M, Gronroos L. "Caries in the Primary Teeth and Salivary *Streptococcus mutans* and Lactobacillus Levels as Indicators of Caries in Permanent Teeth." *Pediatr Dent* (1987) Jun.;9(2):126–30.

Ten Cate JM, Duyster PPE. "Influence Of Fluoride In Solution On Tooth Mineralization.: II Microradiograph Data." *Caries Res* (1983) 17:513–519.

Ten Cate JM, Duyster PPE. "Influence of Fluoride In Solution On Tooth Mineralization: I Chemical Data." *Caries Res* (1983) 17:193–199.

Riordan PJ., "Fluoride Supplements in Caries Prevention: A Literature Review and Proposal for a New Dosage Schedule." *J Public Health Dent* (1993) Summer;53(3):174–89.

Rolla G, Ogaard B, Cruz Rde A. "Clinical Effect and Mechanism of Cariostatic Action of Fluoride–Containing Toothpastes: A Review." *Int Dent J* (1991) Jun.;41(3):171–4.

Stephen KW. "Fluoride Toothpastes, Rinses, and Tablets." (1994) Jul.;8(2):185–9.

Jacob R.C., "Management Of The Irradiated Patient With Xerostomia." *Clin Plast Surg* (1993) 20:507–516.

Levine MJ. "Development of Artificial Salivas." *Crit Rev Oral Biol Med.* (1993) 4(3–4):279–86.

Nielsen AE Toft JM. "Electrolyte Crystal Growth Kinetics." *Journal of Crystal Growth* (1984) 67:278–288.

Van Louveren C., "The Antimicrobial Action Of Fluoride And Its Role In Caries Inhibition." *Journal of Dental Research* (1990) 69:676–68.

Hamilton IR. "Effects of Fluoride on Enzymatic Regulation of Bacterial Carbohydrate Metabolism." *Caries Res* (1977) 11 Suppl 1:262–91.

Hamilton IR, Bowden GH. "Response of Freshly Isolated Strains of *Streptococcus mutans* and *Streptococcus mitior* to Change in pH in the Presence and Absence of Fluoride During Growth in Continuous Culture." *Infect Immun* (1982) Apr.;36(1):255–62.

Hamilton IR, Boyar RM, Bowden GH. "Influence of pH and Fluoride on Properties of an Oral Strain of *Lactobacillus casei* Grown in Continuous Culture." *Infect Immun.* (1985) Jun.;48(3): 664–70.

Sharma M, Dhillon AS, Newbrun E. "Cell–Bound Glucosyltransferase Activity of *Streptococcus Sanguis* Strain 804." *Arch Oral Biol* (1974) Nov.;19(11):1063–72.

Kashket S, Rodriguez VM "Fluoride Accumulation by a Strain of Human oral *Streptococcus Sanguis* ." *Arch Oral Biol* (1976) 21(8):459–64.

Arends J. Ten Cate JM. "Tooth Enamel Remineralization." *Journal of Cyrstal Growth.* (1981) 53:135–147.

Featherstone JD, Glena R, Shariati M, Shields CP. "Dependence of in Vitro Demineralization of Apatite and Remineralization of Dental Enamel on Fluoride Concentration." *J Dent Res.* (1990) Feb.;69 Spec No:620–5; discussion 634–6.

Boyer PD. "The ATP Synthase—A Splendid Molecular Machine." *Ann Rev Biochem* (1997) 66:717–49.

Weber J, Senior AE. Catalytic Mechanism of F1–ATPase. *Biochim Biophys Acta* (1997) Mar. 28;1319(1):19–58.

Ogilvie I, Aggeler R, Capaldi RA "Cross–linking of the Delta Subunit to One of the Three Alpha Subunits Has No Effect on Functioning, as Expected if Delta is a Part of the Stator that Links the F1 and F0 Parts of the *Escherichia coli* ATP Synthase." *J Biol Chem* (1997) Jun. 27;272(26):16652–6.

* cited by examiner

PROTON MOTIVE FORCE TOOTHBRUSH

CROSS REFERENCE TO RELATED APPLICATIONS

This is a non-provisional application having priority to provisional application 60/227,267 filed on Aug. 24, 2000.

FIELD OF THE INVENTION

1. This invention relates to a toothbrush having sufficient means for providing sufficient voltage for electrolysis of dentifrice, gels, and rinses to produce hydronium ions and an aqueous acid media.

BACKGROUND OF THE INVENTION

There is a hydration layer between the enamel of teeth and a natural covering of a glyco-protein adhesive film called a pellicle that is present on all teeth in the oral cavity. This layer of water molecules is vectorial with a positive charge directed toward the oxyanion of the phosphate ion of the apatite crystals of enamel. This vector magnitude insulates the tooth against electrical potentials produced by electrophoresis. Any claim that a potential on teeth by electrophoresis does not take this physico-chemical phenomena into account.

SUMMARY OF THE INVENTION

The present invention uses the phenomena of electrolysis to obtund decay of teeth and periodontal disease. Without limiting the invention to any mechanism, it is believed the production of a weak acid media, using an electromotive force for electrolysis, will react with the fluoride and bicarbonate compounds, if present, of the dentrifice, gels, and rinses in the oral cavity. This is a more organized and active use of these products compared with the random and passive diffusion that occurs when brushing in the absence of this energy. The present invention provides an efficient means to obtund decay and periodontal disease by lowering the count of acid-producing bacteria in plaque. At the same time, the present invention will strengthen the apatite crystal bundles of the hard tissues of teeth and bleach the teeth.

The present invention is a circuit comprising a) a dry cell wafer battery, b) two leads having exposed lead end plates, c) a photovoltaic cell, and d) a rectifying diode. Preferably, the circuit is incorporated in a toothbrush produced by computer-aided injection moulding for precision construction.

DETAILED DESCRIPTION OF THE INVENTION

The present invention system is used to harden impure apatite crystal bundles of dentin and enamel as well as interfering in the synthesis of adenosine triphosphate (ATP). The addition of the fluoride ion present in gels, dentrifice pastes and topical applications to the apatite crystals under the influence of sufficient electromotive force to induce an electrolytic redox reaction which will obtund tooth decay.

While brushing teeth, the two exposed end plates will contact the slurry of saliva, gels, dentifrice, and rinses that contain fluoride and sometimes bicarbonate molecules and with the proper voltage will cause a redox reaction with the water molecules present by electrolysis resulting in the production of weak acids of fluoride and bicarbonate. This acid media will diffuse the protons (i.e., hydrogen ions) present through the cell walls and membranes of bacteria that exist in the oral cavity by mass action. Bacteria need the hydrolysis of ATP to form energy rich metabolites for all vital functions. It is believed the presence of the protons and the fluoride ions in the cytosol of the bacteria will upset the equilibrium of the proton motive force and the flavo-cytochrome transport system necessary for the enzymatic reactions needed for the production of ATP.

The basic reaction of the anode and cathode end plates is one of electrolysis of the water molecules existing in the slurry while brushing the teeth. How the system obtunds tooth decay and periodontitis and the embodiments of the toothbrush will become apparent from the description taken in connection with the accompanying drawings.

The Electrolytic Circuitry

Figure 1:
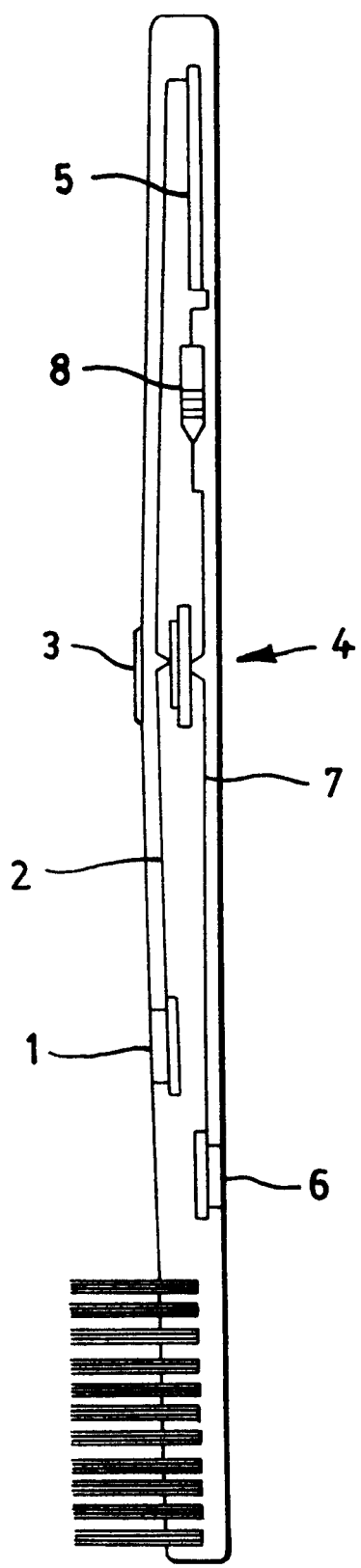
FIG. 1 illustrates a side view of a dielectric toothbrush.

FIG. 1 shows the side view of a toothbrush with an exposed cathode lead contact plate surface 1. The cathode lead 2 enters the handle of the toothbrush and progresses to a cavity 3 with a protective cover (not shown) over it holding the wafer cell battery 4 where it contacts the cathode of the battery. The cathode lead 2 continues and contacts the cathode of the photovoltaic cell 5. FIG. 1 also shows the side view of the toothbrush with the exposed anode lead contact plate surface 6. The anode lead 7 enters the handle of the toothbrush and progresses to a cavity 3 holding the wafer cell battery 4 where it contacts the anode of the battery. The anode lead 7 continues through the cavity and contacts a rectifying diode 8. This diode prevents power leakage during darkness and adds longevity to the battery and in turn, is attached to the anode of the photovoltaic cell 5 wherein said photovoltaic cell revitalizes the battery 4. This completes the circuit of the system which will pump electrons from the cathode plate surface and remove them from the anode contact plate surface.

Figure 2:
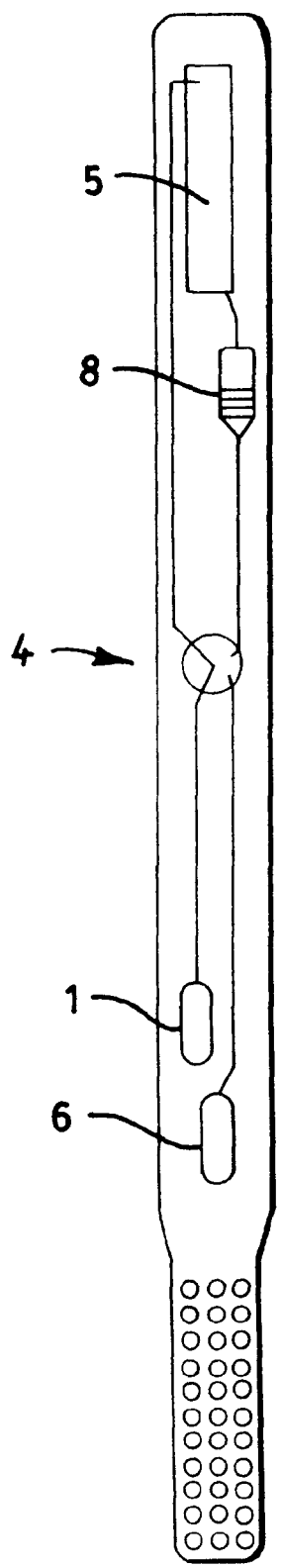
FIG. 2 illustrates a top surface view of a dielectric toothbrush.

FIG. 2 shows a top view of the relative positions of the exposed contact plate surfaces 1 & 6 of the leads 2 & 7 and their contact with the wafer cell battery 4, the anode lead 7 contact with the rectifying diode 8, the rectifying diode contact with the photovoltaic cell 5, the photovoltaic cell contact with the cathode lead 2, and the contact of the cathode lead with the wafer cell battery 4.

Figure 3:
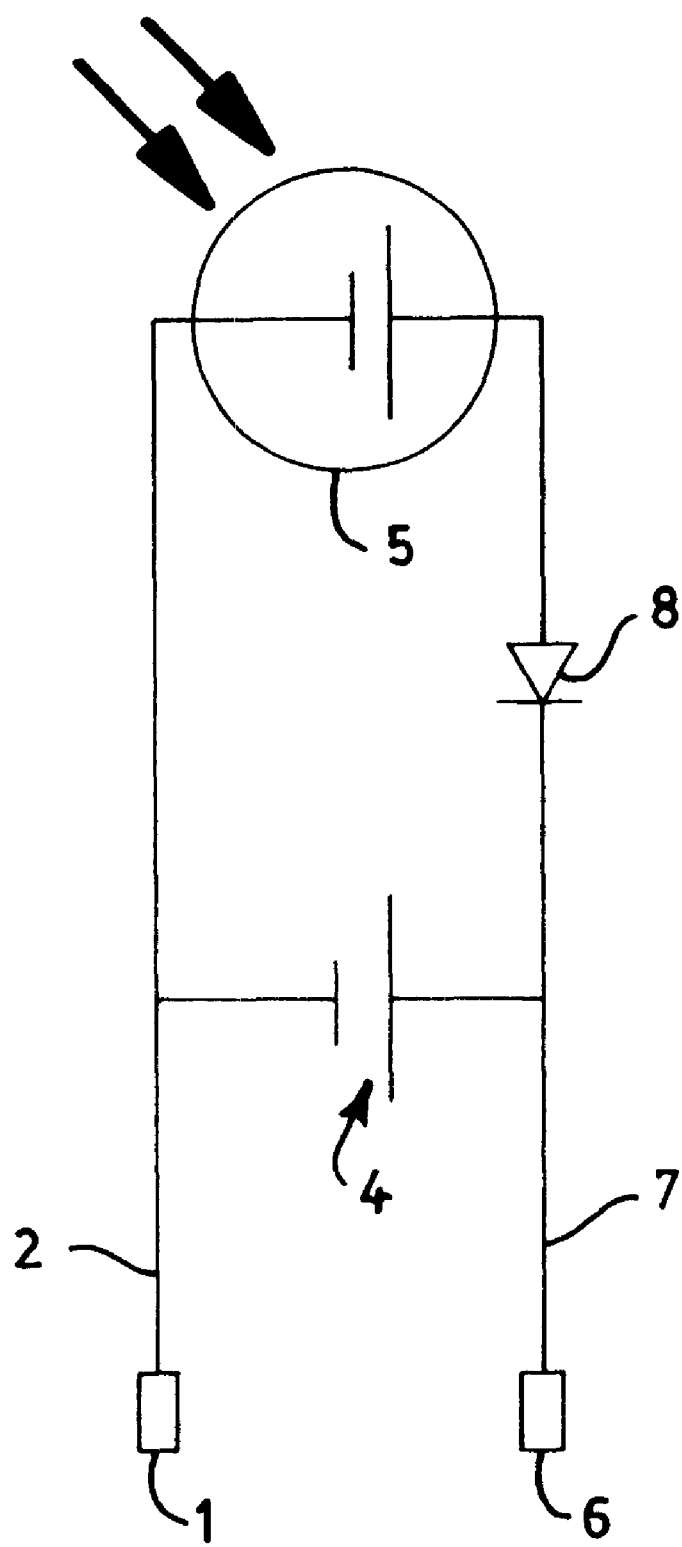
FIG. 3 depicts the circuitry of a dielectric toothbrush.

FIG. 3 is a diagram of the circuitry enclosed in the handle of the toothbrush with the exception of the exposed contact plate surfaces 1 & 6. The arrows represent incident light on photovoltaic cell 5.

The Intracellular Biochemical Reactions

All energy requirements of bacteria are coupled to the hydrolysis of ATP. This energy is used for both exogonic and endogonic reactions that are necessary for cell growth and reproduction. In the cytosol of bacteria oxidized organic compounds generate electrons, metabolites and precursors to a number of lipids, carbohydrates, and proteins. The contents of the cytosol, cell walls, and plasma membranes are made up of these organic compounds. The synthesis of ribose and the dinucleotides from pyrimidine and purine ribosephosphates are essential for DNA, RNA, coenzymes, and ribosomes.

ATP is produced by a two part protein vesicle in the plasma membrane called ATPase or $F_0F_1$. Specifically, the ATPase is composed of a stalk $F_0$ and a knob $F_1$. Protons from outside the membrane are drawn into the stalk $F_0$ section if there is a pH gradient between the cytosol and the environment outside the cell wall next to the plasma membrane. The stalk $F_0$ joins the knob $F_1$ section inside the membrane bathed by the cytosol. The enzyme component of knob $F_1$ will react with adenosine diphosphate (ADP) and $HPO_4^{-2}$ to form ATP.

The protons are produced by metabolic generating cycles in the cytosol which by their redox reactions with coenzyme molecules produce a flow of electrons. The generating cycles are called the Embden-Myerhof pathway of glycolysis, the pyruvate oxidation cycle, and the citric acid cycle. In these generating cycles, coenzyme molecules are reversibly reduced and oxidized and produce a flow of electrons from a more negative potential to a more positive potential. This results in an electrochemical gradient between the inside and outside of the plasma membrane. This change in electric potential releases energy in such a way that protons are pushed outside the cytosol through the plasma membrane to the outside environment. Here the flow of protons results in an acid pH outside the membrane and a low concentration of protons in the cytosol. The resultant pH and electrochemical gradient favors the flow back across the membrane through the stalk $F_0$ and triggers a catalytic reaction of the enzyme $F_1$ to produce ATP from ADP and $HPO_4^{-2}$. The electrons that are transported down the voltage gradient liberate their energy with the resultant formation of more ATP at the ATPase sites in the plasma membrane. This phenomenon is called Proton Motive Force.

The coenzyme system associated with the flow of electrons and protons is called the flavo-cytochrome system of redox phosphorylation. Biochemists refer to this as the electron transfer system (ETS). A series of redox reactions occur beginning with nicotinamide adenosine dinucleotide (NAD$^+$), to flavo-protein (FP), to coenzyme Q (CoQ), to a group of cytochromes that ultimately reduce oxygen to water in aerobic respiration and $SO_3$ to $NH_3$ and $HS^-$ or $H_2S_2$ respectively.

The optimum temperature for bacteria in the oral cavity is 98.6° F. or 37.0° C. which is the average temperature of the oral cavity in humans. The saliva of the oral cavity has an average pH of 7.0 and varies between 6.8 and 8.0. At this optimum temperature and pH biochemists have determined that the proportional relationship of the concentrations of ATP-$HPO_4^{-2}$ is 8-1-8, respectively. The hydrolysis of ATP supplies the energy for the exogonic and the endogonic chemical reactions of the bacterial cells for the metabolism of the organic compounds necessary for growth, development, and reproduction. $Mg^{2+}$ ion and some $Mn^{2+}$ ions are present as chelators and coenzymes and act as chelators to attach to the two oxygen ions next to the purine adenosine of ATP. These are used to couple the hydrolysis of ATP to enzymes in the metabolic cycles of cell metabolism in bacteria.

The thermodynamic formula for Gibbs free energy changes for this chemical reaction can be represented by:

$$\delta\Gamma = \delta\Gamma^0 + \rho T \ln(ADP)(HPO_4)/ADP \quad \text{I}$$

with ln=natural logarithm, T=absolute temperature, P=the gas constant, and $\delta\Gamma$=free standard energy. Substituting the numerical values into the formula:

$$\delta\Gamma = -31^{KJ/Mol} + 8.134 \times 10^{-3KJ/Mol} \times 310° \ln 1 \times 10^{-3}(8 \times 10^{-3})(8 \times 10^{-3}) \quad \text{II}$$

$$\delta\Gamma = -49^{KJ/Mol} \quad \text{III}$$

This represents the free negative energy value of the hydrolysis of ATP used for bacterial processes at 37 degrees C. and pH of 7.0.

In summary, the central role of ATP in metabolism is that energy obtained from lipids, fats, and carbohydrates is stored in ATP. From this storage the hydrolysis of ATP supplies energy to form the organic substances for cell walls, nucleic acids, and the nutritive compounds to sustain life and the reproduction of cells. The ATP itself is synthesized in the integral enzyme complexes of the plasma membrane of bacteria by a series of redox reactions between NAD$^+$, FP, CoQ, and the cytochrome series which biochemists call ETS. This series of redox reactions causes an electrochemical gradient between the inside and outside of the plasma membrane. The change in electrical potential releases energy in such a way that protons are pushed outside the cytosol and establishes an acid pH in the external environment of the bacteria. The protons flow back into the cytosol via $F_0$ and then to $F_1$ and this triggers a catalytic reaction to form more ATP. The electrons liberate their energy by transportation down a voltage gradient causing a flow of protons. This phenomena is called the Proton Motive Force. By disrupting this system it is possible to obtund the bacterial count of acid-producing bacteria.

The Demineralization Process

In order to understand the inventive system, and the reaction process used to obtund decay and periodontal disease, a description of the mineral composition of the apatite crystal structure of dentin and the natural covering of enamel bathed in saliva is necessary.

All healthy teeth have a natural covering consisting of a hydrated glycoprotein adhesive film called a pellicle. The outer-most layer is a disaccharide called sialic acid. Within this layer is a protein section of the film composed of amino acids. For the most part serine, aspartic, glycine and glutamine, and to a lesser extent, other essential acids are present. There is a hydration layer between the pellicle and enamel where sialic acid is hydrolyzed and attracts the cations of the apatite crystals.

The hydration layer is vectorial and the positive portion is directed toward the negatively charged oxyanion of the phosphate section of the apatite crystal. That is, this vector charge insulates the surface of the teeth. The magnitude and direction of the hydration layer is a natural insulator opposing an electrical potential. Any claim that an electrical potential can be placed on a tooth surface does not take this physico-chemical phenomena into consideration.

The hard tissues of enamel and dentin are made of bundles of pure, and impure, apatite and these bundles are the prime target for acid decomposition by bacteria. Pure apatite crystals are represented by the formula $Ca_{10}(PO_4)_6(OH)_2$. In the enamel and dentin of teeth, calcium may be intermittently substituted by cations such as $Na^+$, $Mg^{++}$, $Zn^{++}$ and other cations to a lesser extent. Also, the phosphate anion may be substituted by a carbonate anion. These substituted areas show hexagonal holes which are connected by carbonates and some of the impure substituted regions of the crystals. The impure apatite crystals using sodium as representative of impure cations present can be illustrated as follows: $Na_\alpha Ca_{10-\alpha}(PO_4)_{6-\beta}(OH)_2$.

The present inventive system will be used as an adjunct to the natural processes of immunity and the supersaturated solution of calcium and phosphate ions that exist in the saliva by using the fluoride and bicarbonate compounds within gels, dentrifices, and rinses of over-the-counter dental products used in dental health procedures. The conjugate base fluoride ion is a weaker base than the hydroxyl ion of the apatite crystal and will not react with acids produced by bacteria.

Salivary products, bacterial metabolites and bacteria will eventually cover the pellicle and form a gelatinous mass called plaque. Plaque adheres to pits, fissures and crevices between the teeth and the gums. The enamel surface of teeth displays many features that allow the diffusion of cations, anions and acid products of bacteria entrance. These features include focal holes that contain global proteins, enamel rod boundaries and developmental spaces call the lines of Retzius. The present invention can use these natural features to great advantage to obtund decay and prevent periodontal disease.

The focal holes, the developmental spaces of the lines of Retzius and any enamel imperfection spaces offer diffusion pathways to the weak acid, hydrogen fluoride (HF). This weak acid is an important product of the electrolytic reaction produced by the present invention system.

Tooth decay begins when acid products of bacteria dissolve the apatite crystal bundles of enamel. Sucrose in the diet, under the influence of *Streptococcus mutans*, is converted into a sticky polysaccharide. This material can function as part of plaque structure and also as a food source for bacteria in time of food deprivation. The *S. mutans* ATP, when chelated to $Mg^{2+}$, activates the enzyme glucosyl transferase on the substrate sucrose by hydrolysis to increase the rate of reaction. The *S. mutans* group of bacteria are gram-positive facultative types that coexist with blood cells, ions and immunoglobulins in the saliva. *S. Mutans* creates an acid media in the plaque in which colonies and aggregates of mixed colonies of different bacteria flourish. The predominate bacterial type depends on the pH of the saliva. *S. mutans* also uses sucrose as a substrate for nutrition. With the enzyme hexokinase and the hydrolysis of ATP as an energy source *S. mutans* metabolizes sucrose to glucose and fructose phosphates. These substrates diffuse through the plasma membrane into the cytosol with the aid of the proton motive force (PMF) and the electron transport system (ETS).

As the magnitude of the plaque increases, that is, as it matures, the acid media created by *S. mutans*, and later Lactobacillus, is optimal for the growth of cocci, rods, bacteroides, spirillum, spirochaetes, Veillonella and fusiforms etc. These bacteria contribute to all the dental diseases to which humans are subject. Lactobacillus is a gram-positive anaerobe and flourishes in low oxygen tension of acid media of plaque initiated by *S. mutans* metabolites. Lactobacillus is next in importance to *S. mutans* and uses pyruvate as a substrate to ferment lactic acid.

The acid media of plaque contains not only lactic acid but also, acetic, propionic, succinic, formic and citric acids as a consequence of an active flora of various bacteria. The protons flow into spaces thermodynamically to equalize the pH between the plaque and the enamel. The protons diffuse through plaque into porous enamel and dentin and dissolve the enamel freeing the calcium and phosphate ions of the apatite bundles into the saliva. This acid-mediated demineralization is the first sign of decay.

The Remineralization Process

Saliva in the oral cavity has a physiological pH that varies between 6.8 and 8.0 with buffering components of phosphate ions, peptides and bicarbonates to neutralize the acids produced by bacteria. Saliva is supersaturated with molecular calcium phosphate in equilibrium with $Ca^{2+}$ ions and $PO_4^{3-}$ ions. With the aid of enough fluoride in solution it can remineralize the demineralized enamel and dentin. Commercial over-the-counter dentrifices, gels and rinses containing fluoride rely upon passive diffusion of fluoride ions between the plaque and enamel to arrest decay of teeth. This process is random and compromised by salivary buffers.

The average dentrifice has an alkali metal fluoride concentration of available fluoride ion on the average of 0.15% to 0.22%. The cationic metal fluoride, in the presence of acid plaque and salivary buffers, will increase in concentration according to its solubility product. That is, the molecule will dissociate into a cation and a fluoride ion in the presence of a hydronium ion ($H^+ + HOH = H_3O^+$). The basic conjugate fluoride ion will react with hydronium ion to form HF in aqueous solution. HF is a weak acid and has a low entropy. That is, HF is highly structured, a weak electrolyte and is weakly dissociated. The dissociation constant and reaction formula can be illustrated as:

$$NaF_{aq} = Na^+_{aq} + F^-_{aq} \text{ and} \qquad \qquad IV$$

$$H_3O^+ + F^-_{aq} = HF_{aq} + HOH \qquad \qquad V$$

$$K_a = 6.9 \times 10^{-4} \text{ M. of } HF_{aq} \qquad \qquad VI$$

As the $F^-_{aq}$ reacts with hydronium ion to form $HF_{aq}$, the $NaF_{aq}$ will increase its disassociation according to its solubility product and more $F^-_{aq}$ will react with the hydronium ion. This process is random and compromised by salivary buffers. The present invention will produce more protons to generate hydronium ion and is a more efficient use of fluoride present in a dentrifice, gel or rinse. The present invention will establish a proton gradient in a more efficient manner and a condition of maximum change.

$Na^+_{aq}$(aqueous sodium ion) and $F^-_{aq}$(aqueous fluoride ion) have high standard reduction potentials and will not participate in redox reactions in an aqueous media; water molecules will preferentially participate in the redox reactions.

Water molecules are reduced at a cathode and undergo an oxidation reaction at the anode. Water molecules oxidized at an anode produce diatomic oxygen, hydrogen ions, 2 electrons and have an oxidation potential of 1.229 V. This evolved diatomic oxygen at the anode will bleach the teeth. The overall reaction can be illustrated as follows:

$$2H_2O + 2e = H_2 + 2OH^- \qquad \qquad VIII$$

$$2H_2O = O_2 + 4H^+ + 2e \qquad \qquad X$$

$$E^0 = -0.828 \text{ V} \qquad \qquad IX$$

$$E^0 = -1.229 \text{ V} \qquad \qquad XI$$
TOTAL $$E^0 = -2.057 \text{ V} \qquad \qquad XII$$

Equation XII is the calculated voltage. However, in practice, there is an additional voltage required in reactions involving hydrogen and oxygen of 0.6 V called the overvoltage This means a voltage of at least 2.657 V must be used as the energy source. A 3 V lithium battery or more may be used for this purpose in the present invention.

The hydrogen ions produced at the anode causes an acid region with $H_3O^+$ (i.e., hydronium ions). The hydronium ions will react with hydroxyl ions and the electrophilic fluoride negative ions that are in an aqueous slurry of dentrifice used in oral hygiene. The fluoride negative ions will also react with plaque acids that have been produced by bacteria.

The result of these combinations is a weak acid HF and water, and may be represented symbolically as:

$$F^-_{aq} + H_3O^- = HF + H_2O \qquad \qquad XIII$$

The production of the weak acid HF using the energy of electromotive force is a more efficient manner of using the available fluoride ions present in gels, dentrifices and rinses rather than the random passive diffusion of the fluoride compounds of gels, dentrifices and rinses that are subject to salivary buffers of the oral cavity.

Antibacterial Effects Of Hydrogen Fluoride

This invention uses a circuit in which a battery acts as an electron pump pushing electrons from a cathode contact plate surface and removing them from an anode contact plate surface in a slurry of saliva and gels, dentrifices and rinses containing fluoride compounds and sometimes bicarbonate compounds. At the cathode, ions undergo reduction by accepting electrons. This process is an oxidation-reduction reaction and the system uses electrolysis of water in which the area around the anode becomes acidic and oxygen is evolved. The hydronium ions will react with fluoride ions to form the weak acid hydrogen fluoride ($HF_{aq}$) and this product will obtund decay and prevent periodontitis by upsetting the proton motive force of bacteria. $HF_{aq}$ will also harden teeth by reacting with hydroxy apatite crystals of enamel and dentin. The hydronium ions will react with bicarbonate ions and form the weak acid hydrogen bicarbonate ($H_2CO_3$) which will contribute to an acid pH within the bacterial cytosol and also upset the proton motive force of bacteria.

The aqueous fluoride molecules in dentifrices, gels and rinses exist in random positions when mixed with saliva in the oral cavity. When voltage is applied to this mixture the random positions organize parallel to the electric field and the protons gather at the anode and unite with $F_{aq}^-$ to form the acid HF. This HF will diffuse into the bacterial cytosol by mass action until equilibrium is reached on both sides of the plasma membrane. The cytosol is buffered by $H_2PO_4^-$ (6.84) and $HPO4^{-(12.80)}$ and is relatively basic. The HF will dissociate as $H^{+ions}$ (i.e., positively charged hydrogen ions; protons) and $F_{aq}^{-ions}$ (i.e., aqueous negatively charged fluoride ions). The protons in the cytosol have bypassed the $F_0$ channel and synthesis of ATP will not take place.

The $F_{aq}^{-ions}$ will have an adverse effect on the reproduction and metabolic mechanisms of the bacteria by forming analogues in place of the intermediate metabolic substrates at the active sites of the enzymes. The analogue has the same configuration as the substrate and bonds to the active site. The enzyme is neutralized and can not perform its' function. A notable example is the aconitase enzyme. The $F_{aq}^{ion}$ will join the double bond dehydrated intermediate molecule cis-aconitate to form an analogue. In the citric acid cycle the tertiary alcohol citrate can not be oxidized. A secondary alcohol isocitrate is formed by isomerization which can be oxidized. The addition of fluoride to the cis-aconitate forms an analogue and the enzyme can not function. The result is that the cycle is stopped at that point and the bacteria will not survive.

The $F_{aq}^{-ion}$ will form an analogue with thymidylate synthase and replaces deoxyuridine monophospate which aids in the production of DNA. This will result in disrupting reproduction functions.

As the HF reaches a stage of equilibrium on both sides of the plasma membrane the $f_{aq}^{-ion}$ will effuse out of the cytosol to join protons and form more HF. Some of the $F_{aq}^{-ion}$ will will remain behind and form molecules with the cofactors and chelators $Mg^{++}$, $Mn^{++}$ and $K^+$. These cations are cofactors and chelators for mutase, enolase, and kinase which are used to catalyze reactions of the Embden-Meyerhof anaerobic glycolysis that form phosphoenolpyruvate and phosphoglycerates to form pyruvate. This will result in disrupting the functions of nutrition in bacteria.

Enamel Hardening Effects Of Hydrogen Fluoride

Acids produced by bacteria will demineralize $(CO_3)_\beta$ and non-calcium regions of tooth enamel and dentin. The saliva is supersaturated with calcium and phosphates along with phosphate and bicarbonate buffering systems. The saliva, therefore, neutralizes acids and provides calcium and phosphate ions to replace the dissolved cation and anions of the crystals of dentin and enamel. This process is called remineralization and hardens the enamel and dentin.

During acid production of plaque bacteria, the HF produced by the voltage (EMF) travels through the pellicle to the neutral water covering between the enamel and the pellicle-plaque layers to the enamel surface. The fluoride adheres to the crystals as $CaF_2$ (i.e., calcium difluoride). This speeds up the remineralization by the growth of fluoroapatite crystals (FAP) and the hydroxyapatite crystals of the demineralized regions.

The formula for the demineralization by lactic acid of apatite represents the acid breakdown of apatite crystal follows:

$$Ca_{10}(PO_4)_6(OH)_2 = 10\ Ca_{aq}^{2+} + 6\ (PO_4)_{aq} + 2\ OH_{aq}^- \qquad IX$$

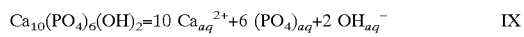

The formula for the lactic acid reaction with the apatite crystal and the products:

$$Ca_{10}(PO_4)_6(OH)_2 + CH_3CHOHCOOH = 3\ Ca_3(PO_4)_6 + 2HOH + (CH_3CHOHCOO)_2Ca \qquad X$$

The production of HF through the influence of the electromotive force (EMF) produced in the present invention will help obtund decay of teeth by strengthening the enamel and dentin crystals. This reaction is represented by the formula:

$$Ca_{10}(PO_4)_6(OH)_2 + 2\ HF = Ca_{10}(PO_4)_6F_2 + 2HOH \qquad XI$$

The aqueous fluoride ion adheres to the crystals and replaces the hydroxyl molecules of the apatite crystals. The fluoride in the form of $CaF_2$ from the saliva will replace the $(CO_3)_\beta$ and non-calcium ion and hydroxyls by adhering to the surfaces also.

Chemically, the $F_{aq}^{-ion}$ is a weaker base than $OH^{-ions}$ and the modified crystal called fluoroapatite (FAP) is more resistant to acids produced by bacteria. Physically, the action of the fluoride ion on the apatite crystal will diminish the distance between the radii of the calcium and the fluoride ions in the crystal. This is according to Van de Waals law of attraction between nuclei. The volume of FAP is less than hydroxylapatite (HAP) and will be more dense as a result and will be less likely to break down under acid attack.

The present invention applies a suitable voltage to fluoride and bicarbonate gels, dentrifices, and rinses to obtund decay of teeth by disrupting the proton motive force of bacterial cells, thereby interfering with the synthesis of ATP. This will destroy the bacteria that produces acid and causes caries (i.e., decay of teeth) and periodontal lesions in the oral cavity.

In addition, the present invention will strengthen the apatite crystals by producing HF more efficiently as a $F_{aq}^{-ion}$ source for adhering fluoride ions to the HAP crystal and as a source of $CaF_2$ for the impure apatite crystals that are of the form:

$$Na_\alpha Ca_{10-\alpha}(PO_4)_{6-\beta}(CO_3)_{[b]\beta}(OH)_2 \qquad XII$$

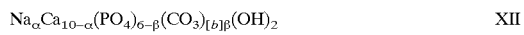

The foregoing description of the inventive system is to be understood as given by illustration and example. The numerous changes and detailed combination and arrangement of parts my be reconstituted without departing from the spirit and scope of the invention as herein claimed.

What is claimed is:

1. A toothbrush, comprising:
   a) a handle incorporating a cathode contact plate and an anode contact plate;
   b) a cathode lead contacting said cathode contact plate, wherein said cathode lead progresses through said handle;
   c) an anode lead contacting said anode contact plate, wherein said anode lead progresses through said handle;
   d) a battery placed within said handle, wherein said cathode lead and said anode lead contact said battery;
   e) a rectifying diode contacting said anode lead, wherein said rectifying diode is on the cathode side of said battery; and
   f) a photovoltaic cell connected to said anode lead and said cathode lead, thereby forming an electromotive circuit.

2. The toothbrush of claim 1, wherein said battery is at least 2.657 V.

3. The toothbrush of claim 2, wherein said battery is a dry cell wafer battery.

4. The toothbrush of claim 1, wherein said cathode contact plate is exposed on said handle.

5. The toothbrush of claim 1, wherein said anode contact plate is exposed on said handle.

* * * * *